United States Patent
Miglio et al.

(10) Patent No.: US 11,162,118 B2
(45) Date of Patent: Nov. 2, 2021

(54) PROCESS FOR THE PRODUCTION OF LIPIDS FROM BIOMASS EMPLOYING OLEAGINOUS YEAST

(71) Applicant: ENI S.P.A., Rome (IT)

(72) Inventors: Roberta Miglio, Oleggio (IT); Daniela Cucchetti, Cuggiono (IT); Valentina Rodighiero, Milan (IT)

(73) Assignee: Eni S.P.A., Rome (IT)

( * ) Notice: Subject to any disclaimer, the term of this patent is extended or adjusted under 35 U.S.C. 154(b) by 590 days.

(21) Appl. No.: 15/126,695

(22) PCT Filed: Apr. 22, 2015

(86) PCT No.: PCT/IB2015/052935
§ 371 (c)(1),
(2) Date: Sep. 16, 2016

(87) PCT Pub. No.: WO2015/162568
PCT Pub. Date: Oct. 29, 2015

(65) Prior Publication Data
US 2017/0088867 A1  Mar. 30, 2017

(30) Foreign Application Priority Data
Apr. 23, 2014  (IT) .......................... MI2014A000761

(51) Int. Cl.
C12P 7/64    (2006.01)
C11B 1/02    (2006.01)
C11B 1/10    (2006.01)

(52) U.S. Cl.
CPC ............. *C12P 7/6463* (2013.01); *C11B 1/02* (2013.01); *C11B 1/025* (2013.01); *C11B 1/10* (2013.01); *Y02E 50/30* (2013.01)

(58) Field of Classification Search
CPC .......... C12P 7/6463; C11B 1/025; C11B 1/02; C11B 1/10; Y02E 50/343; Y02E 50/30
USPC .................................................. 435/134, 41
See application file for complete search history.

(56) References Cited

U.S. PATENT DOCUMENTS

| | | | |
|---|---|---|---|
| 4,888,189 A * | 12/1989 | Gnekow ....................... | 426/231 |
| 5,628,830 A | 5/1997 | Brink | |
| 5,916,780 A | 6/1999 | Foody et al. | |
| 6,090,595 A | 7/2000 | Foody et al. | |
| 6,596,521 B1 * | 7/2003 | Chang et al. ................. | 435/136 |
| 9,234,221 B2 * | 1/2016 | Franzosi et al. .......... | C12P 7/64 |
| 9,885,069 B2 * | 2/2018 | Bortolo et al. ......... | C12P 7/649 |
| 2008/0102176 A1 | 5/2008 | Wu | |
| 2011/0253612 A1 * | 10/2011 | Kale ......................... | C11B 1/10 |
| | | | 210/195.2 |
| 2012/0149076 A1 * | 6/2012 | Granda ................ | B01D 61/022 |
| | | | 435/135 |
| 2013/0289289 A1 | 10/2013 | Franzosi et al. | |

FOREIGN PATENT DOCUMENTS

| | | |
|---|---|---|
| CN | 103314112 A | 9/2013 |
| WO | 2009/063138 A2 | 5/2009 |
| WO | 2009/108773 A2 | 9/2009 |
| WO | 2010/046051 A2 | 4/2010 |
| WO | 2010/069516 A2 | 6/2010 |
| WO | 2010/069583 A1 | 6/2010 |
| WO | 2010/149859 A2 | 12/2010 |
| WO | 2012/042544 A1 | 4/2012 |
| WO | 2012/052368 A1 | 4/2012 |
| WO | 2014/102254 A1 | 7/2014 |

OTHER PUBLICATIONS

Singh, R. "Membrane recycle bioreactors" Chapter 3.1.15 in "Hybrid Membrane Systems of Water Purifcation", 2006, pp. 151-153.

Galafassi, S., et al. "Lipid production for second generation biodiesel by the oleaginous yeast *Rhodotorula graminis*", Bioresource Technology, vol. 111, Feb. 8, 2012, pp. 398-403.

(Continued)

*Primary Examiner* — Satyendra K Singh
(74) *Attorney, Agent, or Firm* — Praedcere Law

(57) ABSTRACT

Process for the production of lipids from biomass including at least one polysaccharide comprising: —subjecting said biomass to hydrolysis to obtain a mixture comprising a first solid phase and a first aqueous phase; —preparing an inoculum comprising at least one oleaginous microorganism in a first fermentation device to obtain a first fermentation broth; —feeding said first aqueous phase and said first fermentation broth to a second fermentation device to obtain a second fermentation broth; —subjecting at least a portion of said second fermentation broth to microfiltration to obtain a first retentate and a first permeate; —feeding said first retentate to said second fermentation device; —subjecting said first permeate to a purification treatment to obtain a second permeate and a second retentate; —feeding said second retentate to said second fermentation device; —at the end of said fermentation, subjecting said second fermentation broth to separation to obtain an aqueous suspension of oleaginous cellular biomass comprising lipids and a second aqueous phase. The lipids thus obtained can advantageously be used in the production of biofuels.

19 Claims, 1 Drawing Sheet

(56) References Cited

OTHER PUBLICATIONS

Dai, et al. "Biodiesel generation from oleaginous yeast *Rhodotorula glutinis* with xylose assimilating capacity", published in the "African Journal of Biotechnology" (2007), vol. 6 (18), pp. 2130-2134.
Humbrid D. et al. in "Technical Report Nrel/Tp-5100-47764" (May 2011).
J. A. Knight et al., "Chemical Basis of the Sulpho-phospho-vanillin Reaction for Estimating Total Serum Lipids", published in "Clinical Chemistry" (1972), vol. 18, No. 3, pp. 199-202.
International Search Report for PCT/IB2015/052935 dated Jul. 8, 2015, 18 pgs.
Office Action in Chinese application No. 201580020241.5 dated Jun. 17, 2020 (Translation in English is provided, 7 pages).

\* cited by examiner

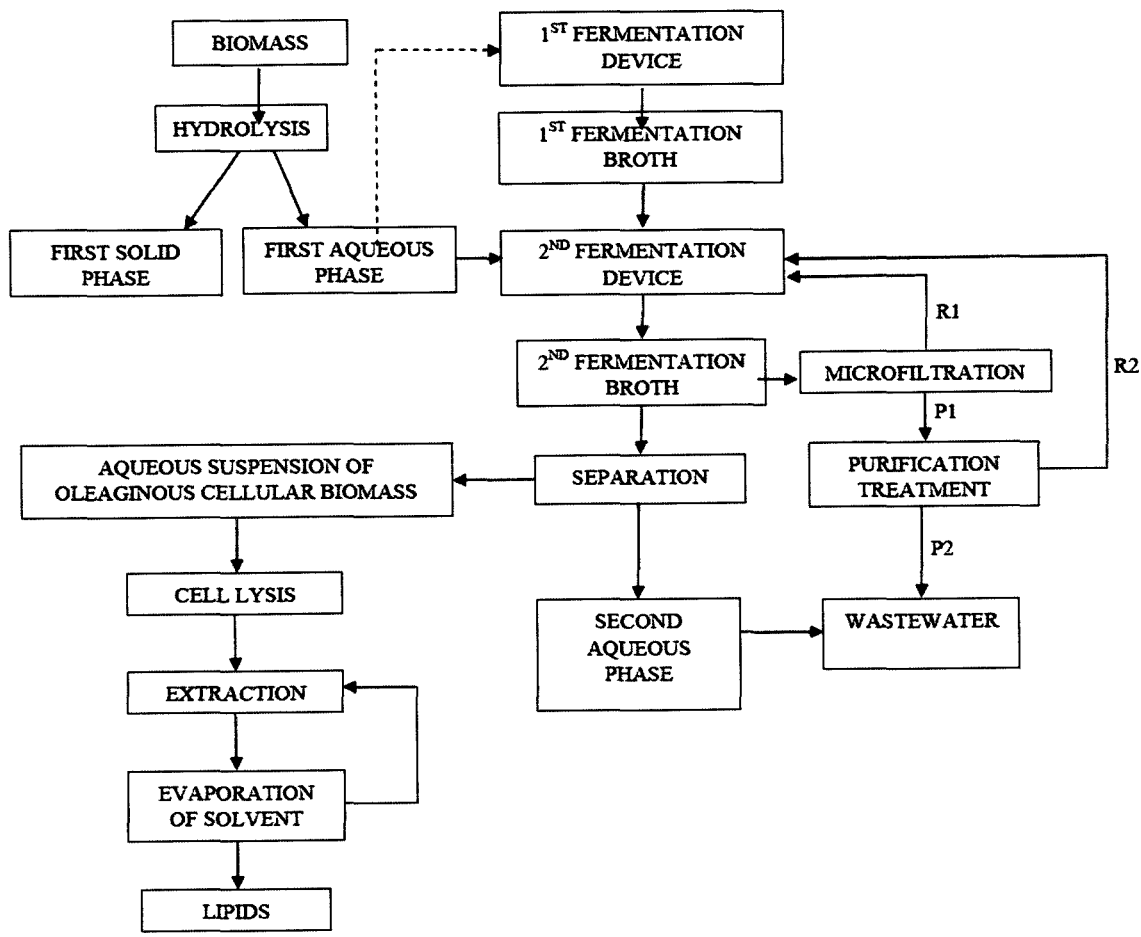

PROCESS FOR THE PRODUCTION OF LIPIDS FROM BIOMASS EMPLOYING OLEAGINOUS YEAST

The present invention relates to a process for the production of lipids from biomass including at least one polysaccharide.

More particularly, the present invention relates to a process for the production of lipids from biomass including at least one polysaccharide comprising subjecting said biomass including at least one polysaccharide to hydrolysis to obtain a mixture comprising a first solid phase and a first aqueous phase; preparing an inoculum comprising at least one oleaginous microorganism in a first fermentation device to obtain a first fermentation broth; feeding said first aqueous phase and said first fermentation broth to a second fermentation device to obtain a second fermentation broth; subjecting at least a portion of said second fermentation broth to microfiltration to obtain a first retentate and a first permeate; feeding said first retentate to said second fermentation device; subjecting said first permeate to a purification treatment to obtain a second permeate and a second retentate; feeding said second retentate to said second fermentation device; at the end of said fermentation, subjecting said second fermentation broth to separation to obtain an aqueous suspension of oleaginous cellular biomass comprising lipids and a second aqueous phase; wherein said microfiltration and said purification treatment are carried out continuously during said fermentation.

The lipids thus obtained can advantageously be used in the production of biofuels, such as, for example, biodiesel or green diesel, which can be used as they are or in a mixture with other fuels for motor vehicles.

In general, biomass is defined as any substance of organic, plant or animal origin which can be used for energy purposes, for example as a raw material for the production of biofuels and/or of biocombustibles, or of components which can be added to fuels and/or to biocombustibles. The biomass may therefore act as a source of renewable energy, as an alternative to the traditional raw materials of fossil origin which are conventionally used in the production of fuels and/or of combustibles. Lignocellulosic biomass is particularly useful for this purpose.

The production of sugars from biomass, in particular from lignocellulosic biomass, is known in the art.

Lignocellulosic biomass is a complex structure comprising three principal components: cellulose, hemicellulose and lignin. The relative quantities thereof vary depending on the type of biomass used. For example, in plants, said quantities vary depending on the species and on the age of the plant.

Cellulose is the major constituent of lignocellulosic biomass, and is generally present in quantities ranging from 30% by weight to 60% by weight based on the total weight of the lignocellulosic biomass. Cellulose consists of glucose molecules (approximately from 500 to 10000 units) linked together by a β-1,4-glucosidic bond. The formation of hydrogen bonds between the chains leads to the formation of crystalline domains that give the plant fibres strength and resilience. In nature, it is only found in the pure form in annual plants such as cotton and flax, whereas in woody plants it is always accompanied by hemicellulose and lignin.

Hemicellulose, which is generally present in quantities ranging from 10% by weight to 40% by weight based on the total weight of the lignocellulosic biomass, is in the form of a relatively short (from 10 to 200 molecules) and branched, mixed polymer formed both from sugars having six carbon atoms (glucose, mannose, galactose) and from sugars having five carbon atoms (xylose, arabinose). Some important properties of said plant fibres are due to the presence of hemicellulose, principal among which is the property of promoting the imbibition of said plant fibres when water is present, causing them to swell. Hemicellulose further exhibits adhesive properties, and therefore tends to cement or take on a horn-like consistency, with the result that said plant fibres become rigid and imbibe more slowly.

Lignin is generally present in quantities ranging from 10% by weight to 30% by weight based on the total weight of the lignocellulosic biomass. The principal function thereof is to bind and cement together the various plant fibres so as to give the plant compactness and strength, and it further forms a protection against insects, pathogens, damages and ultraviolet light. It is principally used as a combustible, but is currently also widely used in industry as a dispersant, hardener, emulsifier, for plastics material laminates, boxes and rubber products. Further, it can also be chemically treated to produce aromatic compounds, such as vanillin, syringaldehyde, p-hydroxybenzaldehyde, which can be used in pharmaceutical chemistry, or in the cosmetic and food industries.

To improve the transformation of lignocellulosic biomass in products for energy use, it is known to subject said lignocellulosic biomass to a preliminary treatment so as to separate the lignin and to hydrolyse the cellulose and the hemicellulose to simple sugars such as glucose and xylose. Said sugars can then be used as a source of carbon in fermentation processes in the presence of microorganisms for the production of alcohols and/or of lipids.

For example, international patent application WO 2009/108773 describes a method for pre-treating a lignocellulosic biomass comprising: pre-treating the lignocellulosic biomass in a first pressurised reactor, wherein the lignocellulosic biomass undergoes hydrolysis; discharging the lignocellulosic biomass from said first pressurised reactor and sending it to a pressurised sealing device having a first pressurised coupling connected to the discharge port of said first pressurised reactor; maintaining a vapour phase in said first pressurised reactor by injecting steam into it, wherein the injected steam provides heat energy to the lignocellulosic biomass; washing the lignocellulosic biomass in a downstream region of said first pressurised reactor or of said pressurised sealing device; draining a liquid including dissolved hemi-cellulose extracted from the lignocellulosic biomass from said first pressurised reactor or from said pressurised sealing device; discharging the lignocellulosic biomass from the pressurised sealing device through a second pressurised coupling to a second pressurised reactor, wherein the lignocellulosic biomass is maintained at a pressure higher than that of the first pressurised reactor; in said second pressurised reactor, infusing cells of the lignocellulosic biomass with steam or water vapour by injecting steam or water vapour into said second pressurised reactor; rapidly releasing the pressure applied to the lignocellulosic biomass infused with water so as to cause steam explosion in the cells of the lignocellulosic biomass and purify the lignocellulosic biomass. Said method makes it possible to obtain sugars which can be used for the production of alcohols (e.g., ethanol).

International patent application WO 2012/042544 describes a composition of biomass comprising a solid, a liquid, an amount of C5 sugars based upon the amount of arabinans and xylans and the monomers, dimers, oligomers and polymers of arabinose and xylose contained in the liquid and solid of the composition, an amount of C6 sugars based upon the amount of glucan, which includes the monomers, dimers, oligomers and polymers of glucan, contained in the liquid and solid of the composition, and furfural, wherein the composition is further characterised as having a 24-hour hydrolytic enzyme accessibility of at least 30%. Said composition is obtained by steam explosion. The sugars obtained after enzymatic hydrolysis can be used for the production of ethanol.

International patent application WO 2009/063138 describes a method of producing lipids or lipid mixtures from organic material comprising a polysaccharide, which is selected from the group comprising cellulose, hemicellulose, starch, all of these, mixtures thereof or degradation products thereof or a non-starch polysaccharide, characterised by comprising: (a) treating the organic material with a substance, which is selected from the group comprising: (i) water, (ii) acid, and (iii) alkali, and subsequently separating the precipitate and filtrate obtained, and subjecting the precipitate obtained from said treatment to mechanical or thermo-mechanical grinding as such or in the presence of water, acid or alkali, and separating the precipitate and the filtrate and, alternatively, subjecting the precipitate one or more times again to the treatment(s) of any of sections (i), (ii) or (iii) and/or grinding, and (b) contacting a lipid-producing microorganism with the filtrate thus obtained or with the various obtained filtrates or with the precipitate, or with any combination thereof and, optionally, with the organic material, in a culture medium, whereby the microorganism cells begin to produce lipid, and (c) recovering the lipids. The lipids obtained by said method can be used in the production of biofuels.

International patent application WO 2010/149859 describes a method for production of fat, characterised in that the method comprises the steps of: contacting, in a cultivation medium, a liquid phase or a residual cell mass or a mixture thereof or any fraction or fractions thereof, obtained by separation, before or after the fat recovery or in connection with the fat recovery, from a single-cell mass obtained from a single-cell oil production process, with a microorganism capable of fat production, and allowing the microorganism to produce fat, and/or contacting, in a cultivation medium, a single-cell suspension or a cell mass obtained from a single-cell oil production process, or a liquid phase obtained from said process, or a microorganism cell suspension obtained in other ways, a cell mass or a liquid phase obtained in said other ways, or mixtures thereof or a fraction or fractions obtained in this manner, with a microorganism capable of fat production, and allowing the organism to produce fat, and recovering the resulting fat or passing the microorganism mass to a single-cell oil production process. The fat obtained by said method can be used in the production of biofuels.

American patent application US 2008/0102176 describes a method for extracting plant fats comprising: pulverizing the cellulose-containing raw material into a plurality of particles of 1-2 mm in diameter; immersing the particles in sulphuric acid of a concentration of 1%-2% to acidify said particles for enhancing the hydrolysis and adjusting the pH value to 4.5±0.5; removing the acidified particles from the sulphuric acid and adding cellulase and oleaginous yeast in sequence to the acidified particles and fermenting for 8-9 days at a temperature of 25° C.-30° C. and a humidity of 85%-90%; adding of aliphatic hydrocarbon as a solvent into the fermentation products to extract fats, thereby obtaining extraction mixture; and removing acidified particles remaining in the extraction mixture and separating the fats from the solvent by distillation to thereby obtain raw oil. Preferably, the cellulase is obtained from *Trichoderma viride* and the oleaginous yeast is *Rhodotorula glutinis*. The fats obtained can be converted into biodiesel after esterification.

Dai et al. describe the production of biodiesel from oleaginous yeast in the article, "Biodiesel generation from oleaginous yeast *Rhodotorula glutinis* with xylose assimilating capacity", published in the "*African Journal of Biotechnology*" (2007), Vol. 6 (18), pp. 2130-2134. In this article, lignocellulosic biomass is ground and subjected to acid hydrolysis in the presence of sulphuric acid. The sugars thus obtained are used as sources of carbon in a fermentation process in the presence of a strain of *Rhodotorula glutinis*, selected in advance, which is also capable of using pentoses, in particular xylose, to obtain oils which are subsequently extracted by Soxhlet extraction and subjected to transesterification to obtain biodiesel.

International patent application WO 2010/046051 describes a process for the production of lipids from biomass including at least one polysaccharide comprising:
  subjecting said biomass to acid hydrolysis in the presence of an aqueous solution of at least one organic acid having from $C_7$ to $C_{20}$ carbon atoms, preferably from $C_9$ to $C_{15}$ carbon atoms, at a temperature ranging from 80° C. to 160° C., obtaining a first mixture comprising a first solid phase and a first aqueous phase,
  subjecting said first mixture to enzymatic hydrolysis obtaining a second mixture comprising a second solid phase and a second aqueous phase,
  subjecting said second aqueous phase to fermentation in the presence of at least one oleaginous yeast obtaining an oleaginous cellular biomass comprising lipids.

The lipids thus obtained can advantageously be used in the production of biodiesel or green diesel, which can be used as they are or in a mixture with other fuels for motor vehicles.

International patent application WO 2012/052368 describes a process for the production of lipids from biomass including at least one polysaccharide comprising:
  subjecting said biomass including at least one polysaccharide to acid hydrolysis obtaining a first mixture comprising a first solid phase and a first aqueous phase;
  feeding said first aqueous phase to a fermentation device in the presence of at least one oleaginous yeast obtaining a first fermentation broth comprising a first oleaginous cellular biomass;
  subjecting said first solid phase to acid hydrolysis or to enzymatic hydrolysis obtaining a second mixture comprising a second solid phase and a second aqueous phase;
  feeding said second aqueous phase to said fermentation device in the presence of said first fermentation broth obtaining a second fermentation broth comprising a second oleaginous cellular biomass including lipids;
  subjecting at least a part of said second fermentation broth to microfiltration obtaining a retentate and a permeate;
  feeding said retentate to said fermentation device.

The lipids thus obtained can advantageously be used in the production of biodiesel or green diesel, which can be used as they are or in a mixture with other fuels for motor vehicles.

Italian patent application MI2012A002249 describes a process for the production of lipids from biomass including at least one polysaccharide comprising:
  subjecting said biomass including at least one polysaccharide to hydrolysis to obtain a mixture comprising a first solid phase and a first aqueous phase;

preparing an inoculum comprising at least one oleaginous microorganism in a first fermentation device to obtain a first fermentation broth;

feeding said first aqueous phase and said first fermentation broth to a second fermentation device to obtain a second fermentation broth;

subjecting said second fermentation broth to separation to obtain an aqueous suspension of oleaginous cellular biomass comprising lipids and a second aqueous phase;

subjecting said second aqueous phase to reverse osmosis to obtain a permeate and a retentate;

feeding said retentate to said first fermentation device or to said second fermentation device, preferably to said first fermentation device.

The lipids thus obtained can advantageously be used in the production of biodiesel or green diesel, which can be used as they are or in a mixture with other fuels for motor vehicles.

Since reducing the process costs for the production of lipids from biomass is of significance, in particular if said lipids are subsequently used in the production of biofuels, such as biodiesel or green diesel, since said biofuels are competing with fossil fuels, which have a lower cost, the study of new processes able to reduce said costs as well as to improve the yield of lipids is still of great interest.

The Applicant has therefore faced the problem of finding a process for producing lipids which are usable in the production of biofuels, such as biodiesel or green diesel, which is able to reduce the process costs as well as to improve the yield of lipids.

The Applicant has now found that the production of lipids from biomass including at least one polysaccharide can advantageously be implemented by a process comprising subjecting said biomass including at least one polysaccharide to hydrolysis to obtain a mixture comprising a first solid phase and a first aqueous phase; preparing an inoculum comprising at least one oleaginous microorganism in a first fermentation device to obtain a first fermentation broth; feeding said first aqueous phase and said first fermentation broth to a second fermentation device to obtain a second fermentation broth; subjecting at least a portion of said second fermentation broth to microfiltration to obtain a first retentate and a first permeate; feeding said first retentate to said second fermentation device; subjecting said first permeate to a purification treatment to obtain a second permeate and a second retentate; feeding said second retentate to said second fermentation device; at the end of said fermentation, subjecting said second fermentation broth to separation to obtain an aqueous suspension of oleaginous cellular biomass comprising lipids and a second aqueous phase; wherein said microfiltration and said purification treatment are carried out continuously during said fermentation.

This process leads to numerous advantages. For example, because said microfiltration and said purification treatment are carried out continuously during said fermentation, said process makes it possible:

to keep the volume of said second fermentation broth in said second fermentation device constant and to increase the concentration of the oleaginous cellular biomass in said second fermentation broth;

to take a part of the water (i.e. first permeate) from said second fermentation broth to remove heat (i.e. a stream at the fermentation temperature is removed and a lower-temperature stream is fed to the fermenter);

to use for said fermentation sugar solutions which are more dilute than normal and available at lower costs;

to recover the sugars as well as the other organic and inorganic substances used in the fermentation (e.g., nitrates, phosphates) which are contained in said first permeate and to recycle them to the fermentation (i.e. second retentate), with resulting lower process costs;

to use a lignocellulosic hydrolysate (i.e. a first aqueous phase) having a higher content of toxic compounds, such as furfural (F), 5-hydroxymethylfurfural (HMF), which may act as inhibitors to the growth of the microorganisms conventionally used in fermentation, and therefore not to have to pay particular attention to the biomass hydrolysis methods;

to work with lower volumes at the end of said fermentation;

to obtain lipids in an increased yield [e.g., a lipids yield greater than or equal to 25% based on the total quantity of sugars used for fermentation, said lipids yield being calculated as grams of lipids obtained per gram of sugar used for fermentation].

Said lipids can advantageously be used in the production of biofuels, such as biodiesel or green diesel, which can be used as they are or in a mixture with other fuels for motor vehicles.

The present invention therefore relates to a process for the production of lipids from biomass including at least one polysaccharide comprising:

subjecting said biomass including at least one polysaccharide to hydrolysis to obtain a mixture comprising a first solid phase and a first aqueous phase;

preparing an inoculum comprising at least one oleaginous microorganism in a first fermentation device to obtain a first fermentation broth;

feeding said first aqueous phase and said first fermentation broth to a second fermentation device to obtain a second fermentation broth;

subjecting at least a portion of said second fermentation broth to microfiltration to obtain a first retentate and a first permeate;

feeding said first retentate to said second fermentation device;

subjecting said first permeate to a purification treatment to obtain a second permeate and a second retentate;

feeding said second retentate to said second fermentation device;

at the end of said fermentation, subjecting said second fermentation broth to separation to obtain an aqueous suspension of oleaginous cellular biomass comprising lipids and a second aqueous phase;

wherein said microfiltration and said purification treatment are carried out continuously during said fermentation.

For the purpose of the present description and of the following claims, the definitions of numerical ranges always include the endpoints unless stated otherwise.

For the purpose of the present description and of the following claims, the term "comprising" also includes the terms "which essentially consists of" or "which consists of".

In a preferred embodiment of the present invention, said polysaccharide may be selected from cellulose, hemicellulose, or mixtures thereof. Cellulose, or mixtures of cellulose and hemicellulose, are particularly preferred.

In a further preferred embodiment of the present invention, said biomass including at least one polysaccharide is a lignocellulosic biomass. As stated above, the lignocellulosic biomass comprises three components: hemicellulose, cellulose and lignin.

Preferably, said lignocellulosic biomass may be selected, for example, from:
- products derived from crops grown specifically for energy use such as *miscanthus*, switchgrass, common reed, including scraps, residues and waste materials from said products or from their processing;
- products derived from agricultural products such as milk thistle, guayule, corn, soybeans, cotton, flaxseed, rapeseed, sugar cane, palm oil, including scraps, residues and waste materials derived from said products or from their processing; products derived from forestry or silviculture including scraps, residues and waste materials from said products or from their processing;
- scraps of food and agricultural products intended for human nutrition or zootechnics;
- non-chemically-treated residues from the paper industry;
- waste materials from separate collection of municipal solid waste (such as municipal plant waste, paper);
- algae such as macroalgae or microalgae, macroalgae in particular.

Preferably, said biomass including at least one polysaccharide may be selected from thistle, guayule, including scraps, residues and waste materials from said thistle or guayule or from their processing.

In a preferred embodiment of the present invention, said biomass including at least one polysaccharide may be subjected to a preliminary procedure of grinding before being subjected to said hydrolysis. Preferably, said biomass including at least one polysaccharide may be ground to obtain particles having a diameter ranging from 0.1 mm to 10 mm, more preferably ranging from 0.5 mm to 4 mm. Particles having a diameter less than 1 mm are particularly preferred.

For the purpose of present invention, the hydrolysis of the biomass including at least one polysaccharide may be carried out by any of the methods known in the art. Non-limiting examples of said methods are:
- heat treatment known as "steam explosion", followed by enzymatic hydrolysis, as described, for example, in the aforementioned international patent application WO 2012/042544;
- treatment in the presence of dilute acids, for example dilute sulphuric acid, followed by enzymatic hydrolysis, as described, for example, by Humbrid D. et al. in "Technical Report Nrel/Tp-5100-47764" (May 2011);
- treatment in the presence of organic acids, for example 2-naphthalenesulphonic acid, followed by enzymatic hydrolysis, as described, for example, in the aforementioned international patent WO 2010/046051.

Said enzymatic hydrolysis may be carried out by methods known in the art as described, for example, in american patents U.S. Pat. Nos. 5,628,830, 5,916,780, 6,090,595, using commercially available enzymes such as for example, Celluclast 1.5L (Novozymes), Econase CE (Rohm Enzymes), Spezyme (Genecor), Novozym 188 (Novozymes), used individually or mixed together.

Said hydrolysis results in a mixture comprising a solid phase and an aqueous phase.

Said mixture is subjected to filtration or centrifugation to obtain a first solid phase and a first aqueous phase.

Said first solid phase comprises lignin and said first aqueous phase comprises at least one sugar having 5 to 6 carbon atoms, more preferably xylose and glucose.

The quantities of sugar obtained after hydrolysis can be determined by techniques known in the art such as, for example, high-performance liquid chromatography (HPLC), or ion exchange chromatography.

In a preferred embodiment of the present invention, said aqueous phase may comprise:
- a quantity of glucose greater than or equal to 50 g/l, preferably greater than or equal to 100 g/l, up to the solubility limit of glucose in said first aqueous phase;
- a quantity of xylose from 0 g/l to 200 g/l, preferably from 10 g/l to 100 g/l;
- a quantity of arabinose from 0 g/l to 20 g/l, preferably from 5 g/l to 10 g/l;
- a quantity of mannose from 0 g/l to 20 g/l, preferably from 2 g/l to 10 g/l;
- a quantity of galactose from 0 g/l to 10 g/l, preferably from 2 g/l to 8 g/l;
- a quantity of acetic acid from 0 g/l to 8 g/l, preferably from 0 g/l to 5 g/l;
- a quantity of furfural (F) from 0 g/l to 2.5 g/l, preferably from 0.1 g/l to 1.5 g/l;
- a quantity of 5-hydroxymethylfurfural (HMF) from 0 g/l to 4.5 g/l, preferably from 0.2 g/l to 3.5 g/l.

However, it should be noted that the process according to the present invention makes it possible to use quantities of toxic compounds, i.e. furfural (F) and 5-hydroxymethylfurfural (HMF), much greater than those normally used, i.e. makes it possible to use a quantity of furfural (F) ranging from 0.1 g/l to 1.5 g/l and a quantity of 5-hydroxymethylfurfural (HMF) ranging from 0.2 g/l to 3.5 g/l.

To obtain said inoculate, beside at least one oleaginous microorganism, at least one aqueous solution comprising a quantity of sugars greater than or equal to 40 g/l, preferably ranging from 45 g/l to 60 g/l, has to be added to said first fermentation device.

In a preferred embodiment of the present invention, in said first fermentation device, the fermentation may be carried out at a temperature ranging from 20° C. to 40° C., preferably ranging from 25° C. to 35° C.

In a preferred embodiment of the present invention, in said first fermentation device, the fermentation may be carried out for a time ranging from 10 hours to 36 hours, preferably ranging from 12 hours to 26 hours.

In a preferred embodiment of the present invention, in said first fermentation device, the fermentation may be carried out at a pH ranging from 4.5 to 7, preferably ranging from 5 to 6.7. To keep the pH in the desired ranges, an aqueous solution of at least one inorganic base, such as, for example, sodium hydroxide, potassium hydroxide, calcium hydroxide, magnesium hydroxide, or mixtures thereof, preferably potassium hydroxide, or at least one inorganic acid, such as, for example, phosphoric acid, sulphuric acid, hydrochloric acid, or mixtures thereof, may be added, in a quantity such as to obtain the desired pH, to the culture medium used for the fermentation.

It should be noted that, in the process according to the present invention, said aqueous solution comprising a quantity of sugar greater than or equal to 40 g/l, preferably ranging from 45 g/l to 60 g/l, may be an aliquot of the first aqueous phase obtained from the hydrolysis of the biomass including at least one polysaccharide, optionally diluted so as to have to desired quantities of sugar.

When the oleaginous microorganism has reached a concentration greater than or equal to 8 g/l, preferably ranging from 10 g/l to 25 g/l, said first fermentation broth, in accordance with the process according to the present invention, is fed to a second fermentation device.

In a preferred embodiment of the present invention, in said second fermentation device, the fermentation may be carried out at a temperature ranging from 20° C. to 40° C., preferably ranging from 25° C. to 35° C.

In a preferred embodiment of the present invention, in said second fermentation device, the fermentation may be carried out for a time ranging from 2 days to 10 days, preferably ranging from 3 days to 8 days.

In a preferred embodiment of the present invention, in said second fermentation device, the fermentation may be carried out at a pH ranging from 4.5 to 7, preferably ranging from 5 to 6.7. To keep the pH in the desired ranges, an aqueous solution of at least one inorganic base, such as, for example, sodium hydroxide, potassium hydroxide, calcium hydroxide, magnesium hydroxide, or mixtures thereof, preferably potassium hydroxide, or at least one inorganic acid, such as, for example, phosphoric acid, sulphuric acid, hydrochloric acid, or mixtures thereof, may be added, in a quantity such as to obtain the desired pH, to the culture medium used for the fermentation.

In a preferred embodiment of the present invention, said microorganism may be selected from oleaginous yeasts such as *Rhodotorula glutinis, Rhodotorula gracilis, Rhodotorula graminis, Lypomices starkeyi, Lypomices lipofer, Trigonopsis variabilis, Candida kefyr, Candida curvata, Candida lipolytica, Torulopsis* sp., *Pichia stipitis, Trichosporon cacaoliposimilis, Trichosporon oleaginosus, Trichosporon pullulans, Rhodosporidium azoricum, Cryptococcus curvatus.*

In a preferred embodiment of the present invention, the fermentation in said second fermentation device may be carried out in one or more stages, in a discontinuous mode ("batch"), in a semi-continuous mode ("fed-batch"), in a continuous mode, in a perfusion mode. Preferably, the fermentation in said second fermentation device is carried out in a discontinuous mode ("batch") for the first 3 hours-10 hours and subsequently in a perfusion mode.

For the purpose of the present description and of the following claims, the term "perfusion mode" means that during fermentation, within said second fermentation device the volume of said second culture broth is kept constant, whilst at least part of the culture medium used for the fermentation is replaced, continuously, with the second retentate deriving from the purification treatment, thus making it possible for the cellular biomass to become concentrated therein. Said "perfusion mode" is implemented by the aforementioned microfiltration, which is actually carried out continuously during fermentation.

In said first fermentation device and in said second fermentation device, which are devices known in the art, the fermentation is carried out in the presence of culture media conventionally used for this purpose, comprising, beside the sugars, various nutrients, such as, for example, nitrogen, potassium phosphate, magnesium, salts, vitamins, microelements To increase the lipids yield, corn steep liquor may be added to said second fermentation device.

In a preferred embodiment of the present invention, said process further comprises adding to said second fermentation device corn steep liquor in a quantity ranging from 2 g/l to 20 g/l, preferably ranging from 4 WI to 18 g/l. Said corn steep liquor may be added both during the feeding of said first aqueous phase and after the feeding of said first aqueous phase.

In a preferred embodiment of the present invention, said microfiltration may be carried out during the exponential (or logarithmic) growth phase of the oleaginous cellular biomass.

For the purpose of the present description and of the following claims, the term "exponential (or logarithmic) growth phase", means the phase in which the oleaginous microorganism used in the fermentation reproduces at a constant speed (corresponding to the maximum reproduction speed) determined both by the genetic characteristics of said oleaginous microorganism and by environmental factors (e.g., temperature, composition of the culture medium). By way of example, for the oleaginous microorganism used in the examples below, i.e. *Rhodosporidium azoricum* RGRDP3, the exponential growth phase ranges from 3 hours to 10 hours.

In a preferred embodiment of the present invention, said microfiltration may be carried out through membranes having a mean pore volume ranging from 0.02 µm to 2.0 µm, preferably ranging from 0.1 µm to 0.8 µm.

In a preferred embodiment of the present invention, said microfiltration may be carried out applying a transmembrane pressure (TMP) ranging from 0.05 bar to 2.5 bar, preferably ranging from 0.1 bar to 2.2 bar.

Said transmembrane pressure (TMP) is calculated in accordance with the following equation:

$$TMP = 0.5*(P_1+P_2)-P_3$$

wherein:
$P_1$=pressure of the aqueous suspension of oleaginous cellular biomass on the input side of the membrane;
$P_2$=pressure of the aqueous suspension of oleaginous cellular biomass at the output side of the membrane;
$P_3$=pressure of the permeate.

It should be noted that for the purpose of the present invention, said transmembrane pressure (TMP) may be obtained using a pump, for example a peristaltic pump, which, when applied to the microfiltration apparatus downstream from the permeate output, lowers the pressure on the output side of the membrane, producing a positive transmembrane pressure (TMP) which generates a flow of permeate.

In a preferred embodiment of the present invention, said microfiltration may be carried out performing at a specific flow (kg of permeate per square metre of surface of the micofiltration membrane per hour) ranging from 0.2 kg/(m²×h) to 70 kg/(m²×h), more preferably ranging from 0.4 kg/(m²×h) to 50 kg/(m²×h).

In a preferred embodiment of the present invention, said microfiltration may be carried out at a temperature ranging from 20° C. to 40° C., preferably ranging from 25° C. to 35° C., more preferably at the fermentation temperature.

In a preferred embodiment of the present invention, said microfiltration may be implemented through flat sheet or hollow fibre polymeric membranes submerged or in tangential configuration ("cross flow"), or through ceramic membranes submerged or in tangential configuration ("cross flow") or in rotating configuration ("dynamic cross flow").

Examples of membranes which may be used for the purpose of the present invention and which are commercially available are "Hydrosart® Microfiltration Cassettes" from Sartorius, Ceram Inside® products from Tami, Schumasiv™ or Membralox® products from Pall, or Microza products from Asahi Kasei Corporation.

For the purpose of the present invention and of the following claims, the term "first retentate" means the aqueous suspension containing concentrated oleaginous cellular biomass deriving from the microfiltration of at least part of said second fermentation broth.

For the purpose of the present invention and of the following claims, the term "first permeate" means the aqueous stream containing sugars and other organic and inorganic substances (e.g., nitrates, phosphates) from the microfiltration of at least part of said second fermentation broth.

In a preferred embodiment of the present invention, said purification treatment may be implemented by means of reverse osmosis, or by evaporation.

In a preferred embodiment of the present invention, said reverse osmosis is carried out in the presence of at least one polymeric membrane that is selected from the polymeric membranes generally used for desalination (usually known as "sea water membranes" or "brackish water membranes") such as, for example: membranes comprising polyamides, polyimides, polysuiphones, polyethersulphones. Preferably, said polymeric membrane is selected from the polymeric membranes comprising polyamides.

In a preferred embodiment of the present invention, said polymeric membrane may have a maximum operating temperature ranging from 15° C. to 90° C., preferably ranging from 20° C. to 80° C., yet more preferably ranging from 20° C. to the fermentation temperature.

In a preferred embodiment of the present invention, said polymeric membrane may have a maximum operating pressure ranging from 5 bar to 80 bar, preferably ranging from 10 bar to 70 bar.

In a preferred embodiment of the present invention, said polymeric membrane may have a molecular weight cutoff (MWCO) ranging from 30 daltons to 200 daltons, preferably ranging from 40 daltons to 100 daltons.

In a preferred embodiment of the present invention, said polymeric membrane may be selected from those having an operating pH compatible with the pH of the first permeate, preferably ranging from 1 to 13, more preferably ranging from 2 to 11, even more preferably ranging from 3.5 to 7.5.

Examples of polymeric membranes which can be used for the purpose of the present invention and which are commercially available are the Dow™ Filmtec™ products of series SW30, series BW30, or series BW30LE, from Dow Chemical, or the Desal™ products of series AG from General Electric, or the TFC®-HR products from Koch Membrane Systems.

The aforementioned polymeric membrane may be in the form of planar discs, tubular membranes, spiralled module membranes, thin film composite (TFC) membranes, or in other useful forms.

In a preferred embodiment of the present invention, said reverse osmosis may be carried out applying a pressure in the feeding side (retentate side) ranging from 5 bar to 80 bar, more preferably ranging from 10 bar to 40 bar.

In a preferred embodiment of the present invention, said reverse osmosis may be carried out by working at a specific flow (kg of permeate per square metre of the surface of the reverse osmosis membrane per hour) ranging from 5 kg/($m^2$×h) to 80 kg/($m^2$×h), more preferably ranging from 10 kg/($m^2$×h) to 40 kg/($m^2$×h).

For the purpose of the present invention and of the following claims, the term "second retentate" means the aqueous stream concentrated in sugars and other organic and inorganic substances (e.g., nitrates, phosphates) deriving from said first permeate. Said aqueous stream concentrated in sugars preferably contains a quantity of sugars ranging from 20 g/l to 110 g/l, more preferably ranging from 30 g/l to 100 g/l.

For the purpose of the present invention and of the following claims, the term "second permeate means the aqueous stream deriving from said first permeate.

In a preferred embodiment of the present invention, said evaporation may be carried out at a temperature ranging from 30° C. to 100° C. and at a pressure that varies depending on the temperature and which is equal to the pressure (vapour pressure) at which the water evaporates at that temperature, preferably at a pressure ranging from 0.04 bar to 1 bar.

It should be noted that if the purification treatment is implemented by evaporation a purified phase (evaporated phase) equivalent to said second permeate and a concentrate equivalent to said second retentate, are obtained.

At the end of the fermentation, to deactivate the lipolytic enzymes (e.g., lipase), said second fermentation broth may be subjected to heat treatment. Said heat treatment may be carried out at a temperature ranging from 70° C. to 120° C., preferably ranging from 75° C. to 110° C., for a time ranging from 5 minutes to 3 hours, preferably ranging from 30 minutes to 2 hours.

At the end of the fermentation, the separation to which the second fermentation broth is subjected to recover said aqueous suspension of oleaginous cellular biomass comprising lipids (said aqueous suspension of oleaginous cellular biomass having a concentration of oleaginous cellular biomass greater than the concentration of oleaginous cellular biomass in said second fermentation broth) and said second aqueous phase (said second aqueous phase optionally containing suspended solids, for example, cells of the oleaginous microorganism used in the fermentation, or particulate deriving from the deterioration of the equipment used in the process, or from the precipitation of salts) may be implemented by methods known in the art, such as, for example, filtration, filter pressing, microfiltration or ultrafiltration, centrifugation.

Said second permeate may be subjected to further treatments for the purpose of being eliminated, or may be recovered and used as process water within the process according to the present invention (for example, as a washing water or dilution water).

For the purpose of further concentrating the aqueous suspension of oleaginous cellular biomass comprising lipids obtained after separation, said aqueous suspension of oleaginous cellular biomass may, before being subjected to recovery of the lipids (i.e. to cell lysis, extraction by solvent and evaporation of the solvent), be subjected to centrifugation. Said centrifugation may be carried out for a time ranging from 5 minutes to 30 minutes, preferably ranging from 15 minutes to 25 minutes, at a rotation speed ranging from 3000 rpm to 9000 rpm, preferably ranging from 4000 rpm to 8000 rpm.

For the purpose of recovering the lipids, said aqueous suspension of oleaginous cellular biomass comprising lipids may be subjected to cell lysis, which may be implemented by various methods. Non-limiting examples of said methods are:

heat treatment, which may be carried out using autoclaves under pressure (for example Brignole autoclave model AU-2, or Parr stirred reactor model PA 4575), at a pressure ranging from 2 bar to 6.5 bar, preferably ranging from 3 bar to 5.5 bar, at a temperature ranging from 100° C. to 160° C., preferably ranging from 110° C. to 150° C., for a time ranging from 1 hour to 8 hours, preferably ranging from 1.5 hours to 4 hours, under stirring ranging from 100 rpm to 800 rpm, preferably ranging from 400 rpm to 600 rpm, as described, for example, in the aforementioned international patent application;

mechanical treatment, which may be carried out using high-pressure homogenisers (for example, Gea Niro-Soavi homogeniser model NS3006L), at a pressure ranging from 800 bar to 2000 bar, preferably ranging from 1000 bar to 1600 bar, at a temperature ranging from 10° C. to 100° C., preferably ranging from 20° C. to 80° C., at a flow rate of the aqueous suspension of oleaginous cellular biomass ranging from 5 l/h to 50 l/h, preferably ranging from 7 l/h to 40 l/h;

microwave treatment, which may be carried out using microwave devices (for example, Milestone microwave device model MicroSYNTH), at a temperature ranging from 45° C. to 150° C., preferably ranging from 50° C. to 100° C., for a time ranging from 10 minutes to 2 hours, preferably ranging from 15 minutes to 1 hour.

At the end of said cell lysis, the lipids can be recovered from the obtained aqueous suspension of exhausted cellular biomass comprising lipids, by extraction using, for example, a reflux extractor.

Said extraction may be carried out in the presence of at least one organic solvent, which may be selected from: non-polar organic solvents such as, for example, iso-octane, n-octane, or mixtures thereof; mixtures of hydrocarbons, such as, for example, naphtha or diesel cuts which may optionally also be derived from the production of green diesel; polar organic solvents such as, for example, methanol, ethanol, iso-propanol, acetone, ethyl acetate, hexane, methyl-tert-butyl ketone, ethyl-tert-butyl ether, or mixtures thereof; or mixtures thereof.

Said extraction may be carried out at a temperature ranging from 20° C. to 200° C., preferably at the boiling point of the solvent used.

Said extraction may be carried out in the presence of a quantity of solvent ranging from 1 time to 6 times, preferably ranging from 1.5 times to 5 times, the volume of the aqueous phase of the aqueous suspension of exhausted oleaginous cellular biomass comprising liquids which is obtained from the cell lysis.

The aqueous suspension of exhausted oleaginous cellular biomass comprising lipids which is obtained after said cell lysis may be subjected to extraction one or more times. Preferably, said aqueous suspension of exhausted oleaginous cellular biomass comprising lipids may be subjected to extraction from 1 time to 5 times, more preferably from 1 time to 3 times.

At the end of the aforementioned extraction, the following two phases are obtained:
(i) an organic phase comprising lipids dissolved in solvent;
(ii) an aqueous phase comprising cellular debris and traces of non-separated lipids.

For the purpose of recovering the lipids, said organic phase (i) is subjected to evaporation to obtain as a residue a high-boiling oil (ia) comprising lipids and a liquid phase containing the solvent which may be recycled to the aforementioned extraction.

The process according to the present invention makes it possible to recover the lipids at an extraction yield ranging from 40% to 99.9%, preferably ranging from 45% to 99%, said extraction yield being calculated based on the total quantity of lipids present in the (dry) oleaginous cellular biomass obtained after fermentation.

Preferably, the lipids comprised in said organic phase (i) are triglycerides, more preferably esters of glycerol with fatty acids having from 14 to 24 carbon atoms, such as palmitic acid, stearic acid, oleic acid, α-linoleic acid, in quantities greater than or equal to 80% by weight, preferably greater than or equal to 90% by weight, based on the total weight of the lipids. Other lipids which may be present in said organic phase (i) are: phospholipids, monoglycerides, diglycerides, free fatty acids, or mixtures thereof.

The total quantity of lipids present in the aqueous suspension of oleaginous cellular biomass obtained after fermentation in said second fermentation device, as well as the total quantity of lipids contained in said high-boiling oil (ia) may be determined by methods known in the art such as, for example, the colorimetric method based on the reaction of the lipids with phosphoric acid and phosphovanillin using, for example, the "total lipid sulpho-phospho-vanillin" kit marketed by Spinreact S.A./S.A.U., Ctra Santa Coloma, 7-E-17176 Sant Esteve de Bas (GI), Spain. Further details regarding said method may be found, for example, in the following article, "Chemical Basis of the Sulpho-phospho-vanillin Reaction for Estimating Total Serum Lipids", J. A. Knight et al., published in "*Clinical Chemistry*" (1972), Vol. 18, No. 3, pp. 199-202.

Said aqueous phase (ii) comprising the cellular debris, in particular proteins and polysaccharides contained in the cellular membrane of the oleaginous microorganism used, may be dehumidified and made use of as fuel, optionally in connection with the lignin deriving from the hydrolysis of the biomass.

Alternatively, said aqueous phase (ii) may be subjected to anaerobic digestion to produce biogas, which may be used for the production of electrical energy, which may also be used to meet the energy requirements of the process according to the present invention.

Alternatively, said aqueous phase (ii) may be subjected to liquefaction to produce bio-oil, as described, for example, in international patent applications WO 2010/069583 or WO 2010/069516.

The lipids obtained by the process according to the present invention may be subjected to esterification in the presence of at least one alcohol having 1 to 4 carbon atoms, preferably methanol, ethanol, and of at least one acid or basic catalyst, in order to produce glycerol and alkyl esters, in particular methyl esters or ethyl esters (biodiesel).

Alternatively, said lipids may be subjected to hydrogenation/deoxygenation in the presence of at least one catalyst in order to produce green diesel. Hydrogenation/oxygenation processes are known in the art and are described, for example, in european patent application EP 1,728,844.

BRIEF DESCRIPTION OF THE DRAWINGS

FIG. 1 illustrates a process according to this disclosure for the production of lipids from biomass that includes at least one polysaccharide, employing an oleaginous microorganism.

FIG. 1 outlines an embodiment of the process according to the present invention. For this purpose, the biomass including at least one polysaccharide (for example lignocellulosic biomass ground in advance) is subjected to hydrolysis (working in accordance with one of the aforementioned methods known in the art) to obtain a mixture comprising a first aqueous phase and a first solid phase including lignin.

Said mixture is subjected to filtration or centrifugation (not shown in FIG. 1) to obtain a first solid phase and a first aqueous phase.

In the meantime, an inoculum is prepared in a first fermentation device using an oleaginous microorganism (e.g., *Rhodosporidium azoricum*) to obtain a first fermentation broth: it should be noted that, as said above, the aqueous solution comprising a quantity of sugars greater than or equal to 40 g/l, preferably ranging from 45 g/l to 60 g/l, may be an aliquot of the first aqueous phase obtained from the hydrolysis of the biomass including at least one polysaccharide, optionally diluted so as to have the desired quantity of sugars (indicated by a dashed line in FIG. 1).

Said first aqueous phase and said first fermentation broth are fed to a second fermentation device in the presence of an oleaginous microorganism (e.g., *Rhodosporidium azoricum*) to obtain a second fermentation broth.

At least part of said second fermentation broth is subjected, continuously during the fermentation, to microfiltration to obtain an aqueous stream containing sugars and other organic and inorganic substances (e.g., nitrates, phosphates) (first permeate—P1), which is subjected to purification treatment (e.g., by reverse osmosis or evaporation), and an aqueous suspension containing concentrated oleaginous cellular biomass (first retentate—R1), which is sent to said second fermentation device.

From the purification treatment are obtained a further aqueous stream (second permeate—P2), which is sent for disposal (wastewater), and a further aqueous stream concentrated in sugars and other organic and inorganic substances (e.g., nitrates, phosphates) (second retentate—R2), which is sent to said second fermentation device. Said microfiltration and said purification treatment are carried out continuously during the fermentation.

At the end of the fermentation, said second fermentation broth is subjected to separation (e.g., by centrifugation) to obtain an aqueous suspension of oleaginous cellular biomass and a second aqueous phase.

Said aqueous suspension of oleaginous cellular biomass is subjected to cell lysis (working in accordance with one of the methods described above), extraction in the presence of a solvent, and subsequent evaporation of the solvent to obtain lipids, whilst said second aqueous phase is sent for disposal (wastewater).

For a better understanding of the present invention and in order to put it into practice, some illustrative, non-limiting examples thereof are given below.

EXAMPLE 1

Composition of the Lignocellulosic Hydrolysate

The lignocellulosic hydrolysate (i.e. "first aqueous phase") used in the following examples was of the following composition: glucose (126 g/l), xylose (87.1 g/l), arabinose (7.5 g/l), mannose (2.9 g/l), galactose (6.5 g/l), acetic acid (4.9 g/l), furfural (F) (1 g/l), 5-hydroxymethylfurfural (HMF) (3 g/l), for a total sugars content of 230 g/l.

The content of furfural (F) and of 5-hydroxymethylfurfural (HMF) was determined by high-performance liquid chromatography (HPLC) using a LichroCART Purospher RP-18 end-capped (240 mm×4 mm; 5 μm) from Merck, provided with a photodiode UV sensor, with flow 0.8 ml/min, temperature 40° C., and phosphoric acid mobile phase at 0.05% in water (eluent A) and acetonitrile+phosphoric acid at 0.05% in water, at a 90/10 vol./vol. ratio (eluent B), using the elution gradient shown in Table 1.

TABLE 1

| Time (min.) | Eluent A (%) | Eluent B (%) |
|---|---|---|
| 0 | 100 | 0 |
| 4 | 94 | 6 |
| 30 | 85 | 15 |

The sugars content was determined by ion exchange chromatography (HPAE-PAD), using a Dionex chromatograph, equipped with a Carbopac PA100 column, with a gradient of sodium hydroxide and sodium acetate as a counter-ion.

The quantitative determination of the organic acids, i.e. acetic acid, was implemented using a DIONEX BIOLC 4000 ion chromatograph linked to a conductivity sensor (PED—"Pulsed Electrochemical Detector"), Ice-AS1 chromatography column (diameter: 9 mm; length: 250 mm), AMMS-ICE suppressor (Anion MicroMembrane Suppressor), injection volume 50 μl, isocratic elution using heptafluorobutyric acid 0.4 mM.

EXAMPLE 2

Preparation of Inoculum Using Hydrolysate (*Rhodosporidium azoricum*)

The inoculum (i.e. first fermentation broth) was prepared using part of the lignocellulosic hydrolysate (i.e. first aqueous phase) described in Example 1.

For this purpose, 22 ml of said lignocellulosic hydrolysate (i.e. first aqueous phase), suitably diluted with water (78 ml) so as to have a final sugars concentration of 50 g/l, were placed in a 500 ml flask, provided with a magnetic stirrer, to which the following were added in succession: 2 g/l yeast extract, 1 g/l $KH_2PO$, 0.05 g/l $MgSO_4.7H_2O$, 0.01 g/l NaCl and 0.01 g/l NaCl: the pH of the mixture obtained was brought to 6 by adding some drops of potassium hydroxide (KOH) 2.5 M. The mixture obtained was sterilised in an autoclave at 80° C., for 45 minutes.

At the end of the sterilisation, the mixture obtained was brought to room temperature (25° C.) and inoculated with cells of *Rhodosporidium azoricum* RGRDP3, which were left to grow for 24 hours at 30° C., under stirring (200 rpm) to obtain a first fermentation broth having a concentration of oleaginous cellular biomass of 23 g/l (dry weight).

EXAMPLE 3

Fermentation of *Rhodosporidium azoricum* (Microfiltration and Reverse Osmosis Carried Out Continuously)

The fermentation test using cells of *Rhodosporidium azoricum* RGRDP3 was carried out in a 20 litre fermenter, working under the following conditions:

0.78 litres of lignocellulosic hydrolysate (i.e. first aqueous phase) as described in Example 1, suitably diluted with water so as to have an initial sugars concentration of 30 g/l;
2.0 g/l of yeast extract;
5 g/l of corn steep solid
5 g/l of $(NH_4)_2SO_4$;
6 g/l of $KH_2PO$;
0.03 g/l of $MgSO_4.7H_2O$;
0.06 g/l of NaCl;
0.06 g/l of $CaCl_2.2H_2O$;
supplied air: flow equal to 1 l/min
temperature: 30° C.
working pH equal to 6, maintained by adding, when necessary, some drops of a potassium hydroxide solution (KOH) 5 M and sulphuric acid ($H_2SO_4$) 10% (v/v);
stirring at 600 rpm-900 rpm, modulated with the flow of air so as to keep the concentration of dissolved oxygen ($DO_2$) above 30% of the saturation value;
initial volume: 6 litres;

inoculum of *Rhodosporidium azoricum* RGRDP3 (i.e. first fermentation broth) obtained as described in Example 2, diluted to 10% (v/v) with the culture medium used for the fermentation so as to start the fermentation with a concentration of oleaginous cellular biomass equal to 2.3 g/l (dry weight).

The fermentation was carried out in a discontinuous mode ("batch") for the first 6 hours and subsequently in a perfusion mode. In this connection, a tangential microfiltration device, provided with a "Hydrosart® Microfiltration Cassettes" microfiltration membrane from Sartorius, was connected to the fermenter via a piston pump, said membrane having a membrane area equal to 0.1 m$^2$ and a mean pore diameter equal to 0.45 µm, for the purpose of removing part of the culture medium (permeate—P1) and of concentrating the second oleaginous cellular biomass (retentate—R1) produced in said second culture broth. For this purpose, said piston pump was actuated continuously, during the fermentation, so as to recirculate the oleaginous cellular biomass and the culture medium in said microfiltration apparatus at a flow rate equal to of 144 l/h, working under the same pH and temperature conditions given above for the fermentation. Said second oleaginous cellular biomass was thus concentrated to obtain a retentate (R1) which was fed continuously to the fermenter (recirculation) and a permeate (P1) which was fed continuously to the reverse osmosis. The permeate (P1) flow rate was controlled within a range of from 61 ml/h to 75 ml/h using a peristaltic pump positioned downstream from the output of the permeate (P1) from the microfiltration apparatus.

In this connection, the reverse osmosis test was carried out using a flat membranes test apparatus, consisting of a cylindrical steel container on the base of which the polymeric membrane was mounted on filtering porous septum which forms the support for the membrane. The container, provided with stirring, may be pressurised to the pressure of 35 bar. The permeate (P2) is filtered through the membrane and was collected in a container positioned below, whilst the retentate (R2) which was left above the membrane was sent, via a flow control valve positioned downstream from said apparatus, to the fermentation device, at a flow rate ranging from 20 ml/h to 25 ml/h.

For the reverse osmosis, the BW30 membrane from Dow Chemical was used, this being a polyamide-based thin film composite (TFC) membrane having the following features:
nominal molecular weight cutoff (MWCO)=50 daltons;
operating pH=2-11;
maximum operating temperature=70° C.;
maximum operating pressure=68 bar.

The permeate (P1) was thus sent to the above-described reverse osmosis device, under stirring at 500 rpm, at a pressure equal to 35 bar.

From the reverse osmosis was obtained a second retentate (R2) containing sugars concentrated by a concentration factor equal to 3: going from an initial sugars content equal to 28 g/l (first permeate—P1) to a sugars content equal to 84 g/l (second retentate—R2).

The sugars content was determined by working as described in Example 1.

Said second retentate (R2) further contained concentrated salts. In fact, the first permeate (P1) had sodium (Na), potassium (K), magnesium (Mg), calcium (Ca), chlorine (Cl) and phosphorus (P) contents equal to 825 ppm, 3186 ppm, 273 ppm, 184 ppm, 320 ppm and 1880 ppm respectively; meanwhile, the second permeate (P2) had sodium (Na), potassium (K), magnesium (Mg), calcium (Ca), chlorine (Cl) and phosphorus (P) contents of 8 ppm, 50 ppm, less than 2 ppm, less than 2 ppm, 25, 4 ppm, and the second retentate (R2) had sodium (Na), potassium (K), magnesium (Mg), calcium (Ca), chlorine (Cl) and phosphorus (P) contents equal to 2440 ppm, 9550 ppm, 820 ppm, 552 pm, 960 ppm and 5640 ppm respectively.

The salts content was determined by inductively coupled plasma mass spectroscopy (ICP-MS). For this purpose, the ICP-MS ELAN DRCe spectrometer from Perkin Elmer was used. The dilution used for the analysis by means of the aforementioned ICP-MS varied depending on the relevant analyte; the sample for analysis was acidified using nitric acid ($HNO_3$) at 2% by volume. The standard solutions used for calibration were prepared by diluting and acidifying certified 1000 ppm aqueous standard solutions.

The flow rate of the supply to the fermenter, in other words of the second retentate (R2) plus fresh hydrolysate, was controlled automatically throughout the duration of the fermentation using a level sensor, in such a way that the volume of the permeate at the output of the microfiltration (P1) was compensated and the volume of the fermentation broth remained constant in the fermenter: said supply was of a sugars concentration of 295 g/l and was composed, as stated above, of the retentate (R2) and of the fresh hydrolysate, which was obtained as described in Example 1 and diluted as described above, in a ratio of 1:2.

Said flow rate was controlled within a range of from 61 ml/h to 75 ml/h so as to have an input quantity of sugars ranging from 22 g/h to 18 g/h to meet the requirements of the oleaginous yeast and to keep a concentration of 30 g/l in the fermenter.

At the end of the fermentation, after 100 hours, a second fermentation broth was obtained having a concentration of oleaginous cellular biomass equal to 68 g/l (dry weight) and a total lipids content equal to 55% by weight (37.4 g/l) based on the dry weight of said oleaginous cellular biomass, the volume within the fermenter (6 l) being kept constant throughout the test.

The total lipids content was determined using the "total lipids sulpho-phospho-vanillin" kit by working as described above. The sugars content was determined by working as described in Example 1.

Said second fermentation broth was subjected to separation by centrifugation at 7000 rpm for 20 minutes to obtain 1.2 kg of oleaginous cellular biomass [408 g (dry weight)–concentration equal to 35% by weight based on the total quantity of oleaginous cellular biomass obtained].

A yield of oleaginous cellular biomass equal to 0.36 g/g based on the substrate consumed ($Y_{X/S}$=g of biomass obtained per g of substrate consumed) and a lipids yield equal to 0.17 g/g based on the substrate consumed ($Y_{L/S}$=g of lipids obtained per g of substrate consumed) were achieved.

EXAMPLE 4

Fermentation of *Rhodosporidium azoricum* (Microfiltration and Evaporation Carried Out Continuously)

The fermentation test using cells of *Rhodosporidium azoricum* RGRDP3 was carried out in a 20 litre fermenter, working under the following conditions:
0.78 l of lignocellulosic hydrolysate (i.e. first aqueous phase) as described in Example 1, suitably diluted with water so as to have an initial sugars concentration equal to 30 g/l;
2.0 g/l of yeast extract;

5 g/l of corn steep solid
5 g/l of $(NH_4)_2SO_4$;
6 g/l of $KH_2PO$;
0.03 g/l of $MgSO_4.7H_2O$;
0.06 g/l of NaCl;
0.06 g/l of $CaCl_2.2H_2O$;
supplied air: flow equal to 1 l/min
working pH equal to 6, maintained by adding, when necessary, some drops of a potassium hydroxide solution (KOH) 5 M and sulphuric acid ($H_2SO_4$) 10% (v/v);
temperature: 30° C.;
stirring at 600 rpm-900 rpm, modulated with the flow of air so as to keep the concentration of dissolved oxygen ($DO_2$) above 30% of the saturation value;
initial volume: 6 litres;
inoculum of Rhodosporidium azoricum RGRDP3 (i.e. first fermentation broth) obtained as described in Example 2, diluted to 10% (v/v) with the culture medium used for the fermentation so as to start the fermentation with a concentration of oleaginous cellular biomass equal to 2.3 g/l (dry weight).

The fermentation was carried out in a discontinuous mode ("batch") for the first 6 hours and subsequently in a perfusion mode. In this connection, a tangential microfiltration device, provided with a "Hydrosart® Microfiltration Cassettes" microfiltration membrane from Sartorius, was connected to the fermenter via a piston pump, said membrane having a membrane area equal to 0.1 m² and a mean pore diameter equal to 0.45 μm, for the purpose of removing part of the culture medium (permeate—P1) and of concentrating the second oleaginous cellular biomass (retentate—R1) produced in said second culture broth. For this purpose, said piston pump was actuated continuously, during the fermentation, so as to recirculate the oleaginous cellular biomass and the culture medium in said microfiltration apparatus at a flow rate of 144 l/h, working under the same pH and temperature conditions given above for the fermentation. Said second oleaginous cellular biomass was thus concentrated to obtain a retentate (R1) which was fed continuously to the fermenter (recirculation) and a permeate (P1) which was fed continuously to the evaporation. The permeate (P1) flow rate was controlled within a range of from 58 ml/h to 70 ml/h using a peristaltic pump positioned downstream from the output of the permeate (P1) from the microfiltration apparatus.

In this connection, the evaporation test was carried out using a rotavapor. The permeate (P1) was therefore sent to the rotavapor and the evaporation was carried out at 38° C. and at a pressure equal to 147 mbar.

The purified phase (P2) (evaporated phase–equivalent to the second permeate) was condensed using a circuit containing cooling water at 15° C., whilst the concentrate (R2) (equivalent to the second retentate) was sent to the fermentation device by means of a piston pump at a flow rate of from 16 ml/h to 20 ml/h.

From the evaporation was obtained a concentrate (R2) containing sugars concentrated by a concentration factor of 3.5: going from an initial sugars content equal to 28 g/l (first permeate—P1) to a sugars content equal to 98 g/l (concentrate—R2).

The sugars content was determined by working as described in Example 1.

Said second concentrate (R2) further contained all of the salts: for confirmation, the conductivity of said purified phase (P2) was measured after condensation, using an MM40+ conductivity meter from Crison, and was found to be less than 0.2 mS/cm.

The flow rate of the supply to the fermenter, in other words of the second concentrate (R2) plus fresh hydrolysate, was controlled automatically throughout the duration of the fermentation using a level sensor, in such a way that the volume of the permeate at the output of the microfiltration (P1) was compensated and the volume of the fermentation broth remained constant in the fermenter: said supply was of a sugars concentration equal to 313 g/l and was composed, as stated above, of the retentate (R2) and of the fresh hydrolysate, which was obtained as described in Example 1 and diluted as described above, in a ratio of 2:5.

Said flow rate was controlled within a range of from 58 ml/h to 70 ml/h so as to have an input quantity of sugars ranging from 22 g/h to 18 g/h to meet the requirements of the oleaginous yeast and to keep a concentration of 30 g/l in the fermenter.

At the end of the fermentation, after 100 hours, a second fermentation broth was obtained having a concentration of oleaginous cellular biomass equal to 67 g/l (dry weight) and a total lipids content equal to 56% by weight (37.5 g/l) based on the dry weight of said oleaginous cellular biomass, the volume within the fermenter (6 l) being kept constant throughout the test.

The total lipids content was determined using the "total lipids sulpho-phospho-vanillin" kit by working as described above. The sugars content was determined by working as described in Example 1.

Said second fermentation broth was subjected to separation by centrifugation at 7000 rpm for 20 minutes to obtain 1.1 kg of oleaginous cellular biomass [402 g (dry weight)–concentration equal to 36% by weight based on the total quantity of oleaginous cellular biomass obtained].

A yield of oleaginous cellular biomass equal to 0.35 g/g based on the substrate consumed ($Y_{X/S}$=g of biomass obtained per g of substrate consumed) and a lipids yield equal to 0.17 g/g based on the substrate consumed ($Y_{L/S}$=g of lipids obtained per g of substrate consumed) were achieved.

EXAMPLE 5

Recovery of Lipids by Cell Lysis (Heat Treatment)

For this purpose, at the end of the fermentation, 1180 ml of the second fermentation broth obtained as described in Example 3, having a concentration of oleaginous cellular biomass equal to 68 g/l (dry weight), were subjected to centrifugation at 7000 rpm, for 20 minutes, to obtain 200 ml of an aqueous suspension of oleaginous cellular biomass having a concentration of oleaginous cellular biomass equal to 350 g/l (dry weight) and 980 ml of exhausted fermentation water (i.e. second aqueous phase).

The 200 ml of said aqueous suspension were placed in a 0.5 l autoclave (Parr stirred reactor model PA 4575 A) and were brought to a temperature of 140° C., at the autogenous pressure of 4.9 bar, with stirring at 450 rpm, and kept in these conditions for 2 hours. After this time, the exhausted oleaginous cellular biomass was discharged and the extraction process was started (Example 8).

EXAMPLE 6

Recovery of Lipids by Cell Lysis (Mechanical Treatment)

For this purpose, at the end of the fermentation, 6 l of the second fermentation broth obtained as described in Example 3, having a concentration of oleaginous cellular biomass equal to 68 g/l (dry weight), were subjected to centrifugation at 7000 rpm, for 20 minutes, to obtain 200 ml of an aqueous suspension of oleaginous cellular biomass having a concentration of oleaginous cellular biomass equal to 352 g/l (dry weight) and 5.8 l of exhausted fermentation water (i.e. second aqueous phase).

The 5.8 l of said aqueous suspension were pumped in a homogeniser (Gea NiroSoavi model NS3006L) at a homogenising pressure of 1500 bar, at room temperature and at a flow rate of approximately 15 l/h.

At the end of the treatment, the exhausted oleaginous cellular biomass was discharged and the extraction process was started (Example 8).

EXAMPLE 7

Recovery of Lipids by Cell Lysis (Microwave Treatment)

For this purpose, at the end of the fermentation, 1180 ml of the second fermentation broth obtained as described in Example 3, having a concentration of oleaginous cellular biomass equal to 68 g/l (dry weight), were subjected to centrifugation at 7000 rpm, for 20 minutes, to obtain 200 ml of an aqueous suspension of oleaginous cellular biomass having a concentration of oleaginous cellular biomass equal to 350 g/l (dry weight) and 980 ml of exhausted fermentation water (i.e. second aqueous phase).

The 200 ml of said aqueous suspension were placed in a 300 ml glass flask provided with refrigerant, magnetic stir bar, and were brought to a temperature of 100° C. using a microwave device (Milestone model "MicroSYNTH"). The temperature was kept constant for 20 minutes, at atmospheric pressure.

At the end of the treatment, the exhausted oleaginous cellular biomass was discharged and the extraction process was started (Example 8).

EXAMPLE 8

Extraction by Solvent

For the purpose of recovering the lipids contained in the oleaginous cellular biomass obtained after the treatments described in Examples 5, 6 and 7, various extraction tests were performed using various types of solvents or mixtures thereof.

For this purpose, 200 ml of the aqueous suspension of exhausted oleaginous cellular biomass, obtained as described in Example 5, in Example 6 or in Example 7, were used in the various tests.

Said aqueous suspension was subjected to two extraction cycles, each of 2 hours, at the boiling point of the solvent or of the mixture of solvents used, in a reflux extractor, in the presence of a volume of solvent or of mixture of solvents 2 times the volume of said aqueous suspension.

The lipids were obtained after separating the organic phase containing the solvent and the lipids from said aqueous suspension containing the exhausted oleaginous cellular biomass, and after subjecting said organic phase to distillation of the solvent, which is recycled to the extraction.

The solvents and the mixtures of solvents used, the treatments to which the oleaginous cellular biomass was subjected (Examples 6-8—cell lysis), the extraction temperatures and the extraction yields, are shown in Table 2.

TABLE 2

| Treatment | Treatment conditions | Extraction solvent | Extraction temperature | Extraction yield* (%) |
|---|---|---|---|---|
| Heat | autoclave, 140° C., 2 hours | hexane/iso-propanol (3:2; v/v) | 60° C. | 98% |
| Heat | autoclave, 140° C., 2 hours | ethyl acetate | 72° C. | 95% |
| Heat | autoclave, 140° C., 2 hours | iso-octane | 82° C. | 74% |
| Heat | autoclave, 140° C., 2 hours | xylene | 93° C. | 87% |
| Heat | autoclave, 140° C., 2 hours | ethyl tert-butyl ether | 68° C. | 83% |
| Heat | autoclave, 140° C., 2 hours | methyl iso-butyl ketone | 90° C. | 97% |
| Heat | autoclave, 140° C., 2 hours | iso-octano + 10% ethanol | 70° C. | 82% |
| Mechanical | Homogeniser, 1500 bar, 15 l/h | ethyl acetate | 72° C. | 71% |
| Microwave | microwave reactor, 100° C., 20 min. | ethyl acetate | 72° C. | 80% |

*the extraction yield (%) of lipids obtained from the extraction is given based on the total quantity of lipids present in the (dry) oleaginous cellular biomass obtained after fermentation, determined using the "total lipids sulpho-phospho-vanillin" kit by working as described above.

The invention claimed is:

1. Process for the production of lipids from biomass including at least one polysaccharide comprising:
   subjecting said biomass including at least one polysaccharide to hydrolysis to obtain a mixture comprising a first solid phase and a first aqueous phase;
   separating said first aqueous phase from said mixture;
   preparing an inoculum comprising at least one oleaginous microorganism in a first fermentation device and conducting fermentation to obtain a first fermentation broth;
   feeding said first aqueous phase and said first fermentation broth to a second fermentation device and conducting fermentation in said second fermentation device to obtain a second fermentation broth;
   continuously subjecting a portion of said second fermentation broth to microfiltration to obtain a first retentate and a first permeate;
   continuously feeding said first retentate back to said second fermentation device;
   continuously feeding said first permeate to reverse osmosis or evaporation treatment to obtain a second permeate and a second retentate;
   feeding said second retentate back to said second fermentation device along with optional other liquid at a rate so as to maintain a level of liquid in said second fermentation device;
   wherein fermentation in said second fermentation device is carried out in the presence of said first retentate and said second retentate in batch mode followed by a perfusion mode, so as to increase the concentration of lipids; and
   at an end of said fermentation in said second fermentation device carried out in the presence of said first retentate and said second retentate, once lipids concentration has increased to a particular level, subjecting said second fermentation broth to separation to obtain an aqueous suspension of oleaginous cellular biomass comprising said lipids and a second aqueous phase.

2. Process according to claim 1, wherein said polysaccharide is selected from cellulose, hemicellulose, or mixtures thereof.

3. Process according to claim 1, wherein said biomass including at least one polysaccharide is a lignocellulosic biomass, selected from:
products derived from crops grown specifically for energy use;
products derived from agricultural products;
products derived from forestry or silviculture;
scraps of food and agricultural products intended for human nutrition or zootechnics;
non-chemically-treated residues from the paper industry;
waste materials from separate collection of municipal solid waste; or
algae.

4. Process according to claim 1, wherein said biomass including at least one polysaccharide is subjected to a preliminary procedure of grinding before being subjected to said hydrolysis to obtain particles having a diameter ranging from 0.1 mm to 10 mm.

5. Process according to claim 1, wherein said first aqueous phase comprises:
a quantity of glucose from 50 g/l to the solubility limit of glucose in said first aqueous phase;
a quantity of xylose from 0 g/l to 200 g/l;
a quantity of arabinose from 0 g/l to 20 g/l;
a quantity of mannose from 0 g/l to 20 g/l;
a quantity of galactose from 0 g/l to 10 g/l;
a quantity of acetic acid from 0 g/l to 8 g/l;
a quantity of furfural (F) from 0 g/l to 2.5 g/l; and
a quantity of 5-hydroxymethylfurfural (HMF) from 0 g/l to 4.5 g/l.

6. Process according to claim 1, wherein in said first fermentation device, the fermentation is carried out according to at least one of the following:
at a temperature ranging from 20° C. to 40° C.;
for a time ranging from 10 hours to 36 hours;
and at a pH ranging from 4.5 to 7.

7. Process according to claim 1, wherein in said second fermentation device, the fermentation is carried out according to at least one of the following:
at a temperature ranging from 20° C. to 40° C.;
for a time ranging from 2 days to 10 days; and
at a pH ranging from 4.5 to 7.

8. Process according to claim 1, wherein said oleaginous microorganism is an oleaginous yeast selected from the group consisting of *Rhodotorula glutinis, Rhodotorula gracilis, Rhodotorula graminis, Lypomices starkeyi, Lypomices lipofer, Trigonopsis variabilis, Candida kefyr, Candida curvata, Candida lipolytica, Torulopsis* sp., *Pichia stipitis, Trichosporon cacaoliposimilis, Trichosporon oleaginosus, Trichosporon pullulans, Rhodosporidium azoricum*, and *Cryptococcus curvatus*.

9. Process according to claim 1, wherein said process comprises adding to said second fermentation device corn steep liquor in a quantity ranging from 2 g/l to 20 g/l.

10. Process according to claim 1, wherein said microfiltration is carried out during the exponential growth phase of said oleaginous microorganism used in said fermentation in said second fermentation device.

11. Process according to claim 1, wherein said microfiltration is carried out through membranes having a mean pore volume ranging from 0.02 μm to 2.0 μm.

12. Process according to claim 1, wherein said microfiltration is carried out according to at least one of the following:
applying a transmembrane pressure (TMP) ranging from 0.05 bar to 2.5 bar;
performing at a specific flow ranging from 0.2 kg/(m²×h) to 70 kg/(m²×h); and
at a temperature ranging from 20° C. to 40° C.

13. Process according to claim 1, wherein said microfiltration is implemented through flat sheet or hollow fiber polymeric membranes submerged or in tangential configuration, or through ceramic membranes submerged or in tangential configuration or in rotating configuration.

14. Process according to claim 1, wherein said reverse osmosis is carried out in the presence of at least one polymeric membrane of a type that is generally used for desalination.

15. Process according to claim 14, wherein said at least one polymeric membrane has at least one of the following:
a maximum operating temperature range ranging from 15° C. to 90° C.;
a maximum operating pressure ranging from 5 bar to 80 bar;
a nominal molecular weight cutoff (MWCO) ranging from 30 daltons to 200 daltons; and
an operating pH compatible with the pH of the first permeate.

16. Process according to claim 1, wherein said reverse osmosis is carried out by at least one of the following:
applying a pressure at a retentate side ranging from 5 bar to 80 bar; and
operating at a specific flow ranging from 5 kg/(m²×h) to 80 kg/(m²×h).

17. Process according to claim 1, wherein said evaporation is carried out at a temperature ranging from 30° C. to 100° C. and at a pressure.

18. Process according to claim 1, wherein said biomass including at least one polysaccharide is a lignocellulosic biomass from crops grown specifically for energy use selected from: *miscanthus*, switchgrass, or common reed, including scraps, residues and waste materials from said crops, and scraps, residues and waste materials from processing said crops.

19. Process according to claim 1, wherein said biomass including at least one polysaccharide is a lignocellulosic biomass from agricultural products selected from: milk thistle, guayule, corn, soybeans, cotton, flaxseed, rapeseed, sugar cane or palm oil, including scraps, residues and waste materials from said agricultural products, and scraps, residues and waste materials from processing said agricultural products.

* * * * *